(12) United States Patent
Pan (10) Patent No.: US 8,279,410 B2
(45) Date of Patent: Oct. 2, 2012

(54) OPTICAL MEASUREMENT INSTRUMENT FOR BODY HEIGHT (75) Inventor: Weichao Pan, Zhongshan (CN)

(73) Assignee: Zhongshan Transtek Electronics Co., Ltd, Zhongshan, Guangdong (CN)

(*) Notice: Subject to any disclaimer, the term of this patent is extended or adjusted under 35 U.S.C. 154(b) by 467 days.

(21) Appl. No.: 12/524,225

(22) PCT Filed: Jan. 4, 2008

(86) PCT No.: PCT/CN2008/000032
§ 371 (c)(1),
(2), (4) Date: Jul. 23, 2009

(87) PCT Pub. No.: WO2008/092359
PCT Pub. Date: Aug. 7, 2008

(65) Prior Publication Data
US 2010/0103405 A1 Apr. 29, 2010

(30) Foreign Application Priority Data
Jan. 24, 2007 (CN) .......................... 2007 1 0026620

(51) Int. Cl.
G01C 5/00 (2006.01)
(52) U.S. Cl. .................... 356/3.05; 356/3.08; 356/27
(58) Field of Classification Search ............... 356/3.05, 356/3.08, 4.08, 11, 27
See application file for complete search history.

(56) References Cited

U.S. PATENT DOCUMENTS

| 4,336,855 A | * | 6/1982 | Chen ........................... 177/245 |
| 4,518,052 A | * | 5/1985 | Chen ........................... 177/245 |
| 7,327,442 B1 | * | 2/2008 | Fear et al. .................... 356/4.08 |
| 2003/0169901 A1 | * | 9/2003 | Pavlidis et al. ............... 382/103 |
| 2005/0216124 A1 | * | 9/2005 | Suzuki ......................... 700/253 |

* cited by examiner

Primary Examiner — Luke Ratcliffe
Assistant Examiner — Isam Alsomiri
(74) Attorney, Agent, or Firm — Michael G. Johnston; Moore & Van Allen PLLC (57) ABSTRACT

An optical body height measurement instrument is provided comprising: a lens configured to be movable along a direction parallel to the height of an object to be measured and form an image of the object; a photosensitive sensor arranged at an image side of the lens to sense the image; and a driving device configured to drive the lens along a direction parallel to the height of the object, wherein when the lens is moved across the height at which the head of the object is located, a hop occurs to an output of the photosensitive sensor; and wherein the height of the object is determined based on the height of the lens measured at the time of the occurrence of the hop. The optical body height measurement instrument can rapidly, conveniently and accurately measure the height based on the infrared rays emitted from the measured object or the light with a predetermined wavelength emitted from an auxiliary light source so long as the person to be measured stands within a certain region.

10 Claims, 9 Drawing Sheets

OPTICAL MEASUREMENT INSTRUMENT FOR BODY HEIGHT

CROSS-REFERENCE TO RELATED APPLICATIONS

The present application is a National Stage application of International Application No.: PCT/CN2008/000032 filed on Jan. 4, 2008, which claims the benefit of Chinese Patent Application No.: 200710026620.2 filed on Jan. 24, 2007, the contents of both of which are hereby incorporated by reference herein in their entireties.

FIELD OF THE INVENTION

The present invention relates to body height measurement, and in particular to an instrument for optically measuring a body height.

BACKGROUND OF THE INVENTION

There are many methods and apparatus for measuring height. The simplest one among them may be to directly measure the height by means of a ruler. With the development of science and technology, a great variety of advanced height measurement instruments have been developed. It is observed that the advance heads toward digitalized measurements, which are rapid, convenient and more accurate. For example, the conventional ultrasound height measurement instruments measure the height utilizing the time difference between transmission of an ultrasound wave and reception of the echo of the ultrasound wave reflected when directed onto the object to be measured. However, when using such an ultrasound height measurement instrument to measure height, the ultrasound transmitter or the object that reflects the ultrasound wave needs to be placed on the head of the measured object. Therefore, these height measurement instruments have to contact the measured object, which causes great inconvenience to the measurement.

SUMMARY OF THE INVENTION

The object of the present invention is to provide an optical body height measurement instrument which can measure the height rapidly and accurately so long as the object to be measured stands within a certain region. To achieve this object, the following technical solutions are employed.

According to a first aspect of an embodiment of the present invention, there is provided an optical body height measurement instrument comprising: a lens configured to be movable along a direction parallel to the height of an object to be measured and form an image of the object; a photosensitive sensor arranged at an image side of the lens to sense the formed image; and a driving device configured to drive the lens along a direction parallel to the height of the object, wherein when the lens is moved across the head of the object, a hop occurs to an output of the photosensitive sensor; and wherein the height of the object is determined based on the height of the lens measured at the time of the occurrence of the hop change.

When the lens is moved across the height at which the head of the object or the auxiliary light source is located, the photosensitive sensor starts to or not to detect formation of an image of the object or the auxiliary light source, which causes a hop change.

Preferably, the lens forms an image based on infrared rays emitted from the object, and the photosensitive sensor is adapted to sense the infrared image of the object.

Optionally, the optical body height measurement instrument also comprises an auxiliary light source placed on the head of the object to be measured, wherein the lens is configured to form an image of the auxiliary light source. When the lens is moved across the height at which the auxiliary light source is located, a hop occurs to an output of the photosensitive sensor and thus the height of the measured object is determined based on the height of the lens measured at the time of the occurrence of said hop change and a distance between the auxiliary light source and the head of the object.

Preferably, the auxiliary light source emits light with a predetermined wavelength, which is correspondingly sensed by the photosensitive sensor.

More preferably, the auxiliary light source further comprises a contact switch configured to be closed to activate the auxiliary light source when the auxiliary light source is placed on the head of the measured object.

Further preferably, the optical body height measurement instrument also comprises a filter arranged in an optical path between the object and the photosensitive sensor such that only infrared rays emitted from the object or light with a predetermined wavelength emitted from the auxiliary light source are allowed to pass.

Further preferably, the lens comprises at least one convex lens, or the lens is in the form of a pinhole or a slit.

Further preferably, the photosensitive sensor is arranged at the intersection of the imaging plane of the lens and the optical axis of the lens.

Further preferably, the optical body height measurement instrument also comprises a processing unit for computing the height of the object.

Further optionally, the optical body height measurement instrument comprises a display unit for displaying the measured results.

According to a second aspect of an embodiment of the present invention, there is also provided an optical body height measurement instrument comprising: at least two lenses spaced apart along a direction parallel to the height of an object to be measured; and photosensitive sensors arranged in an image side of each of the lens, wherein the at least two lenses are used to form images of the head of the object, and the height of the object is determined based on the height of the lens and the distances between the tops of the images of the head of the object and the optical axes of the lenses obtained from the photosensitive sensor.

Preferably, the lenses form images based on infrared rays emitted from the object, and the photosensitive sensors are adapted to sense the infrared images of the object.

Optionally, the optical body height measurement instrument comprises an auxiliary light source configured to be placed on the top of the head of the object, wherein the at least two lenses form images of the auxiliary light source, and the height of the object is determined based on the distances between the images of the auxiliary light source and the optical axes obtained from the photosensitive sensor, the heights of the lenses, and the distance between the auxiliary light source and the head of the object.

Preferably, the auxiliary light source emits light with a predetermined wavelength, which is then correspondingly detected by the photosensitive sensors.

More preferably, the auxiliary light source further comprises a contact switch configured to be closed to activate the auxiliary light source when the auxiliary light source is placed on the head of the object.

Further optionally, the optical body height measurement instrument also comprises a driving device for driving the lenses to move along the direction parallel to the height of the object.

More preferably, the optical body height measurement instrument comprises a filter arranged in the optical paths between the object and the photosensitive sensors such that only infrared rays emitted from the object or the light with a predetermined wavelength emitted from the auxiliary light source are allowed to pass.

Further preferably, the lens comprises at least one convex lens, or the lens is a pinhole or a slit.

Further preferably, the photosensitive sensors are arranged on the image planes of the lenses.

Further preferably, the at least two lenses are arranged on the same straight line in a direction parallel to the height of the object, with the optical axes thereof parallel to each other.

Further preferably, the photosensitive sensors are composed of a single row or an array of photosensitive units.

Further optionally, the optical body height measurement instrument also comprises a processing unit for computing the height of the measured object.

More optionally, the optical body height measurement instrument comprises a display unit for displaying the measured height.

The advantageous effects of the instruments according to the present invention are in that they can rapidly, conveniently and accurately measure the height based on the infrared rays emitted from the object or the light with a predetermined wavelength emitted from the auxiliary light source so long as the person to be measured stands within a certain region.

BRIEF DESCRIPTION OF DRAWINGS

The present invention will be further explained below in conjunction with the accompanying drawings and preferred embodiments.

DETAILED DESCRIPTION OF THE INVENTION

Embodiment 1

Figure 1:
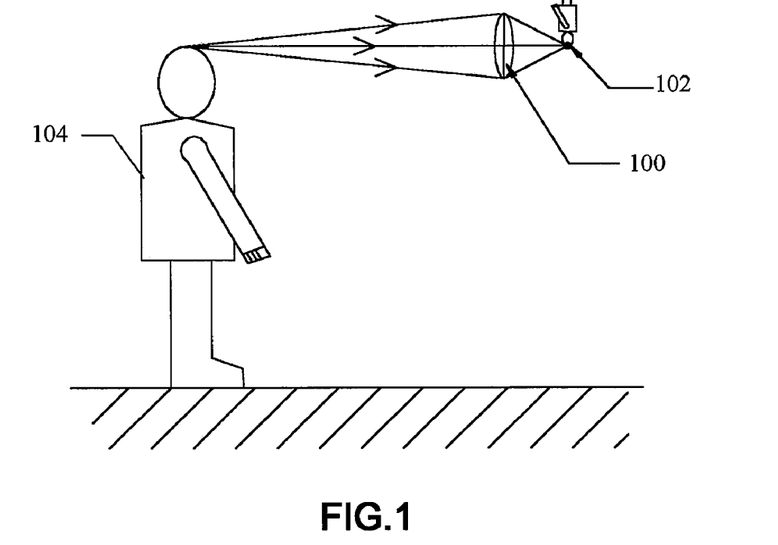
FIG. 1 is a schematic diagram of the optical body height measurement instrument according to an embodiment of the present invention, in which the optical axis of the lens is at the same height as the head of the object to be measured.

As shown in FIG. 1, the optical height measurement instrument according to this embodiment comprises a lens 100 and a photosensitive sensor 102. The lens 100 may be, but not limited to, a convex lens. Alternatively, the lens 100 may be in the form of a pinhole or a slit positioned horizontally. The lens 100 can be driven by a driving device (not shown) to move in the direction parallel to the height of the object 104 to be measured, and can image the object 104. The photosensitive sensor 102 may be arranged at the image side of the lens 100. In this embodiment, it is arranged at the intersection of the image plane and the optical axis of the lens 100 to sense the formed image.

Figure 2:
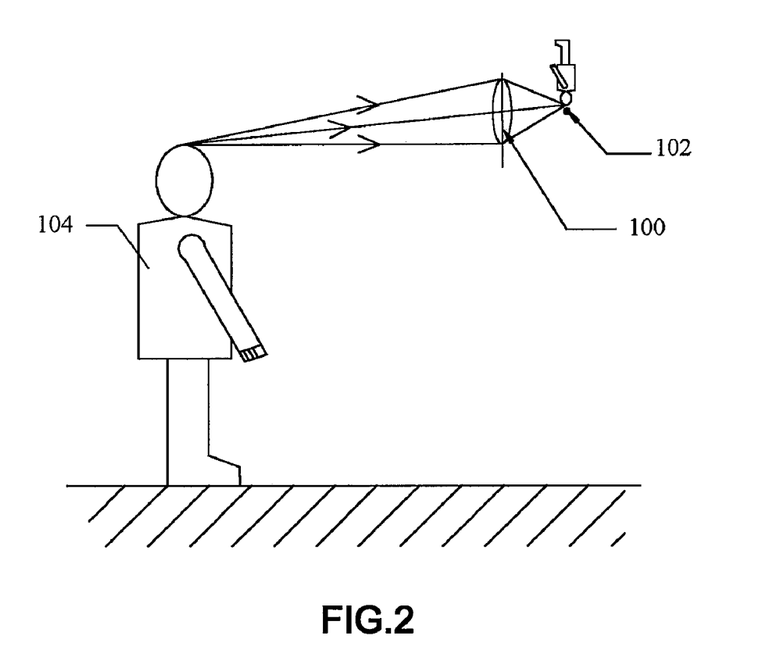
FIG. 2 is a schematic diagram of the optical body height measurement instrument according to an embodiment of the present invention, in which the optical axis of the lens is higher than the head of the object to be measured.
Figure 3:
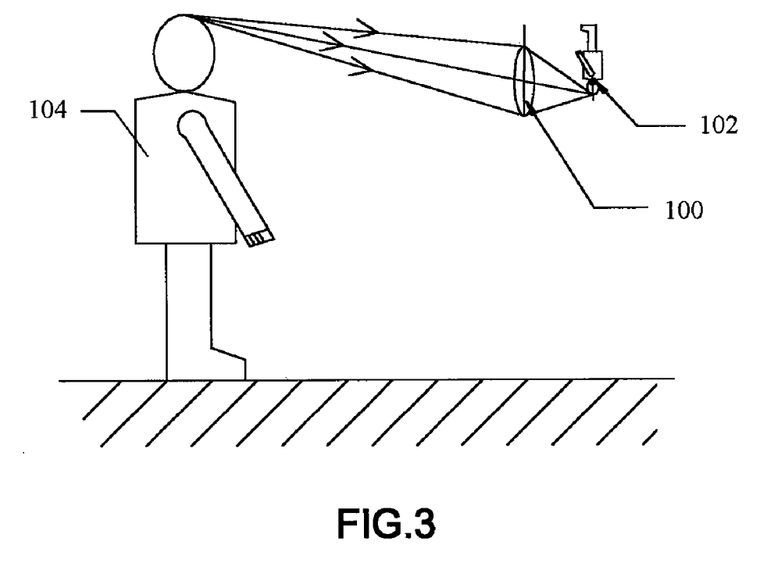
FIG. 3 is a schematic diagram of the optical body height measurement instrument according to an embodiment of the present invention, in which the optical axis of the lens is lower than the top of the head of the object to be measured.

As shown in FIG. 2, the lens 100 is moved upwards from the initial position. When the optical axis of the lens 100 is higher than the head of the object 104 to be measured, the photosensitive sensor 102 can not sense the image of the object 104. On the contrary, when the lens 100 is moved downwards to be lower than the head of the object 104 to be measured, the photosensitive sensor 102 can sense the image of the object 104, as shown in FIG. 3. That is, when the lens 100 moves across the height at which the head of the object to be measured is located, the status of the photosensitive sensor 102 will be subjected to a significant "hop" change. In this case, the height of the optical axis of the lens 100 may be determined as the height of the object to be measured.

In this embodiment, the lens 100 forms images using infrared rays emitted from the object 104 to be measured. The photosensitive sensor 102 then senses the infrared image of the object to be measured. If the initial position of the photosensitive sensor 102 is lower than the height of the object to be measured, infrared rays emitted from the object 104 pass the lens 100 to form an image on the photosensitive sensor 102. The photosensitive sensor 102 then transmits the signal sensed to a processing unit. In response to receiving the signal, the processing unit causes the driving device to move the lens 100 upwards in synchronization with the photosensitive sensor 102. Accordingly, the image of the object 104 changes with its position relative to the optical axis of the lens 100. When the photosensitive sensor 102 is moved to a position at the same height as the head of the object to be measured, the infrared image of the object 104 goes beyond the range sensible to the photosensitive sensor 102. That is, the photosensitive sensor 102 fails to receive any infrared rays emitted from the measured object 104. In accordance with the variation in the status of the photosensitive sensor 102, the processing unit controls the driving device in a manner to stop the lens 100 from continuing moving upwards. Besides, based on the position of the lens 100 at the moment when the sensing status of the photosensitive sensor 102 starts to significantly change, the height of the object 104 can be determined.

In a similar manner, if the photosensitive sensor 102 is higher than the object 104 at its initial position, the infrared rays emitted from the object 104 will not be captured on the photosensitive sensor 102 after passing the lens 100. When this happens, the driving device will cause the lens 100 to move downwards in synchronization with the photosensitive sensor 102 until the photosensitive sensor 102 becomes as high as the object 104, and the infrared rays emitted from the object 104 start to be received by the photosensitive sensor 102. At this point of time, the processing unit controls the driving device to stop the downward movement of the lens 100, and computes the height of the object 104 based on the position of the lens 100 at the moment when the status of the photosensitive sensor 102 starts to significantly change.

Since the dimension of the photosensitive sensor 102 in the vertical direction directly affects the accuracy of the measurement, a reduced dimension will be preferable. Generally, the photosensitive sensor is sized about 0.1 mm in the vertical direction. Of course, the measurement accuracy is also related to the accuracy of the driving device. Therefore, to obtain an accurate height measurement, a stepper motor is employed, or the length of travel of the driving device is measured using a proper mechanism.

The advantageous effect of the measurement instrument according to the embodiment is that it does not have to come into contact with the object to be measured. Instead, as long as the object to be measured stands within a certain region, this instrument will be able to obtain the height of the object rapidly, accurately and more conveniently.

Figure 4:
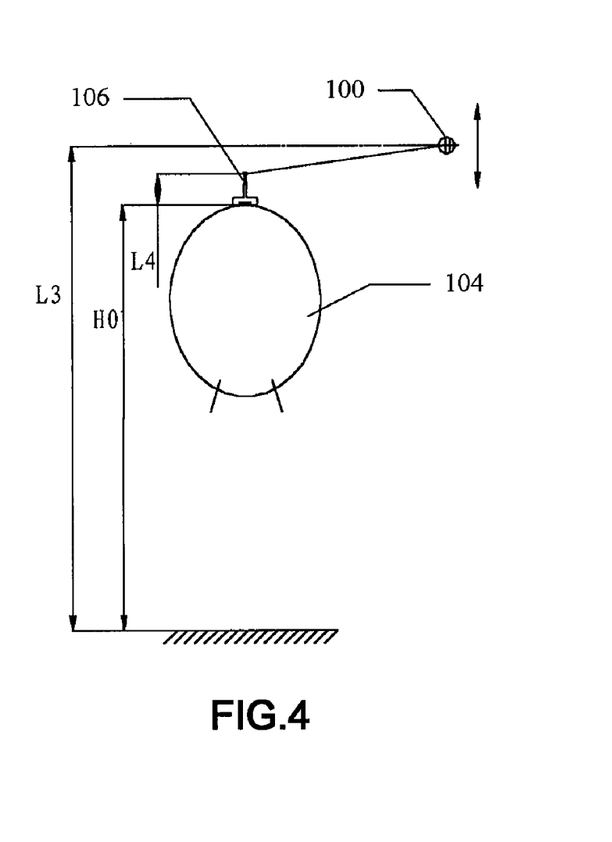
FIG. 4 is a schematic diagram of an optical body height measurement instrument using an auxiliary light source, according to an embodiment of the present invention.
Figure 5:
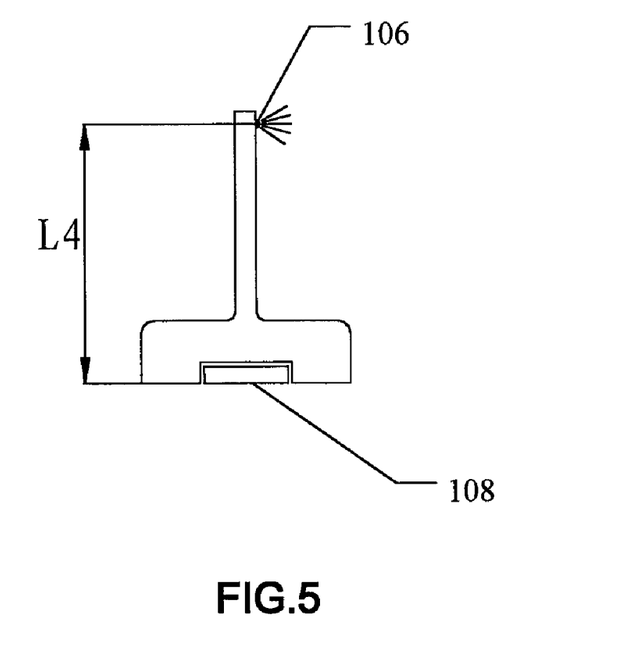
FIG. 5 is a structural schematic diagram of an auxiliary light source according to an embodiment of the present invention.

The body height measurement instrument according to the embodiment optionally comprises an auxiliary light source 106. During the measurement, the auxiliary light source 106 is placed on top of the object 104 to be measured where the lens 100 images the auxiliary light source 106. As shown in FIG. 4, the auxiliary light source 106 emits light with a predetermined wavelength, which is then detected by the photosensitive sensor 102. As shown in FIG. 5, the auxiliary light source 106 may optionally comprise a contact switch 108 which is closed to activate the auxiliary light source 106 when the auxiliary light source 106 is placed on top of the object 104 to be measured.

Figure 6:
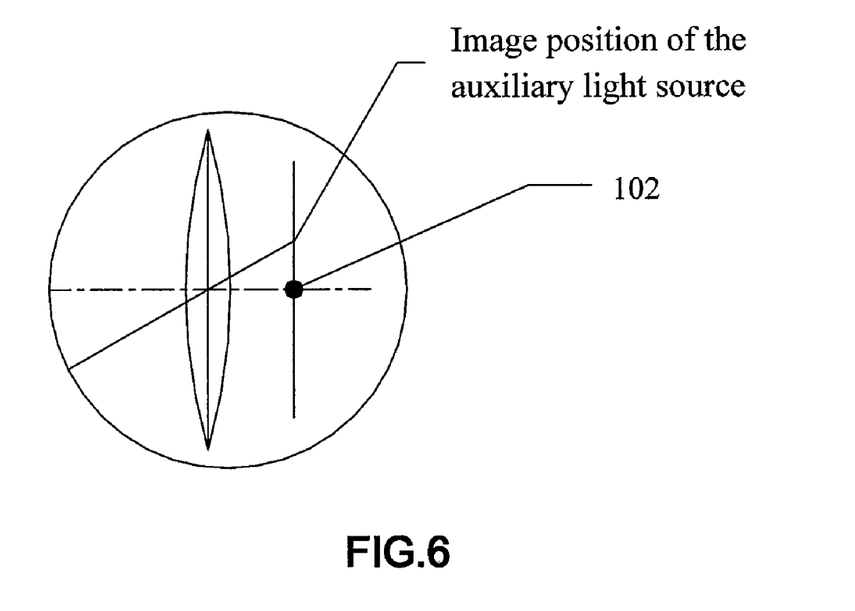
FIG. 6 is a schematic diagram illustrating an image position of the auxiliary light source when the optical axis of the lens is higher than the height at which than the auxiliary light source is located.
Figure 7:
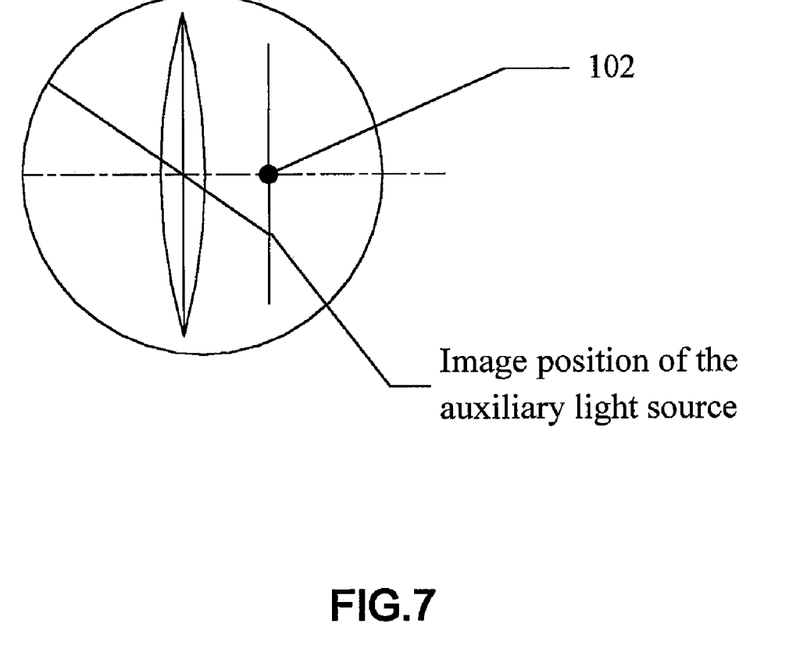
FIG. 7 is a schematic diagram illustrating an image position of the auxiliary light source when the optical axis of the lens is lower than the height at which the auxiliary light source is located.
Figure 8:
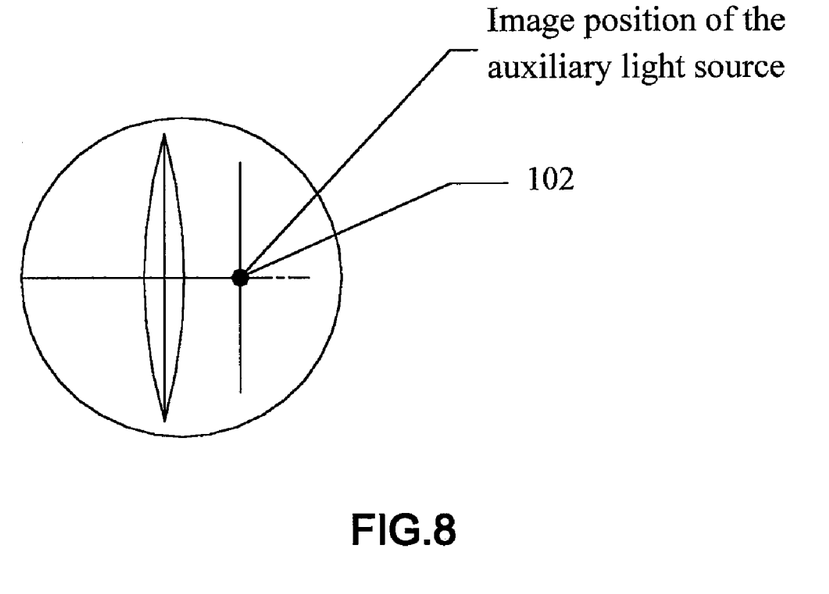
FIG. 8 is a schematic diagram illustrating the image position of the auxiliary light source when the optical axis of the lens is at the same height as that of the auxiliary light source.

As shown in FIG. 6, when the lens 100 is moved upwards to a position where the optical axis of the lens 100 is higher than the position at which the auxiliary light source 106 is located, the image of the auxiliary light source 106 will be formed above the optical axis of the lens 100. Thus, the photosensitive sensor 102 can not sense the image of the auxiliary light source 106. As shown in FIG. 7, when the lens 100 is moved downward to a position where the optical axis of the lens 100 is lower than the auxiliary light source 106, the image of the auxiliary light source 106 will be formed beneath the optical axis of the lens 100. Likewise, the photosensitive sensor 102 can not sense the image of the auxiliary light source 106, either. As shown in FIG. 8, when the optical axis of the lens 100 is at the same height as the auxiliary light source 106, the image of the auxiliary light source 106 is formed right on the optical axis of the lens 100. Thus, the photosensitive sensor 102 can sense the image of the auxiliary light source 106. That is, when the lens 100 moves across the height at which the auxiliary light source 106 is located, a significant "hop" change will occur to the status of the photosensitive sensor. In this case, length L4 of the auxiliary light source 106 is subtracted from height L3 of the lens 100 to give the height of the object to be measured.

Figure 9:
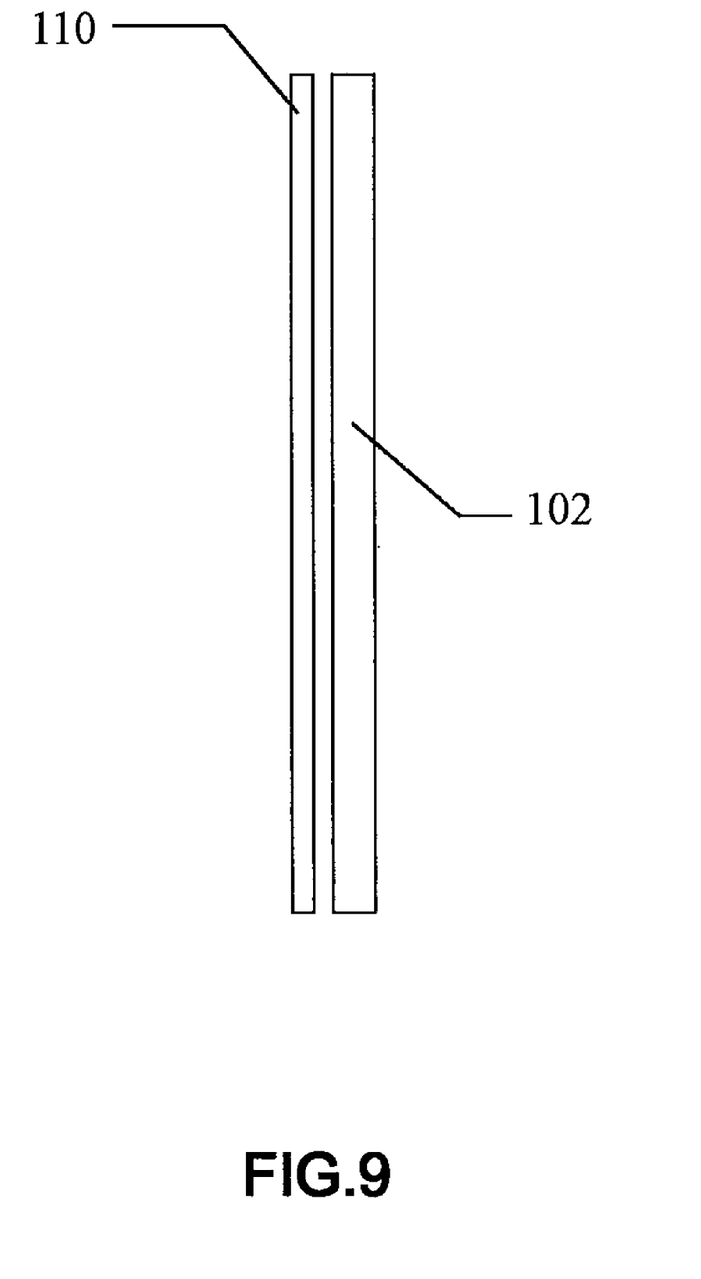
FIG. 9 is a schematic diagram illustrating the position of the filter relative to the photosensitive sensor.

To reduce interference, a filter 110 may be arranged in the optical path between the object 104 to be measured or the auxiliary light source 106 and the photosensitive sensor 102, so that only the infrared rays emitted from the object 104 or the light with a predetermined wavelength emitted from the auxiliary light source 106 are allowed to pass. In this embodiment, the filter 110 is preferably arranged in front of the photosensitive sensor 102, as shown in FIG. 9.

The height measurement instrument according to the embodiment may further comprise a display unit 116 coupled to the processing unit to display the measurement results.

Embodiment 2

Figure 10:
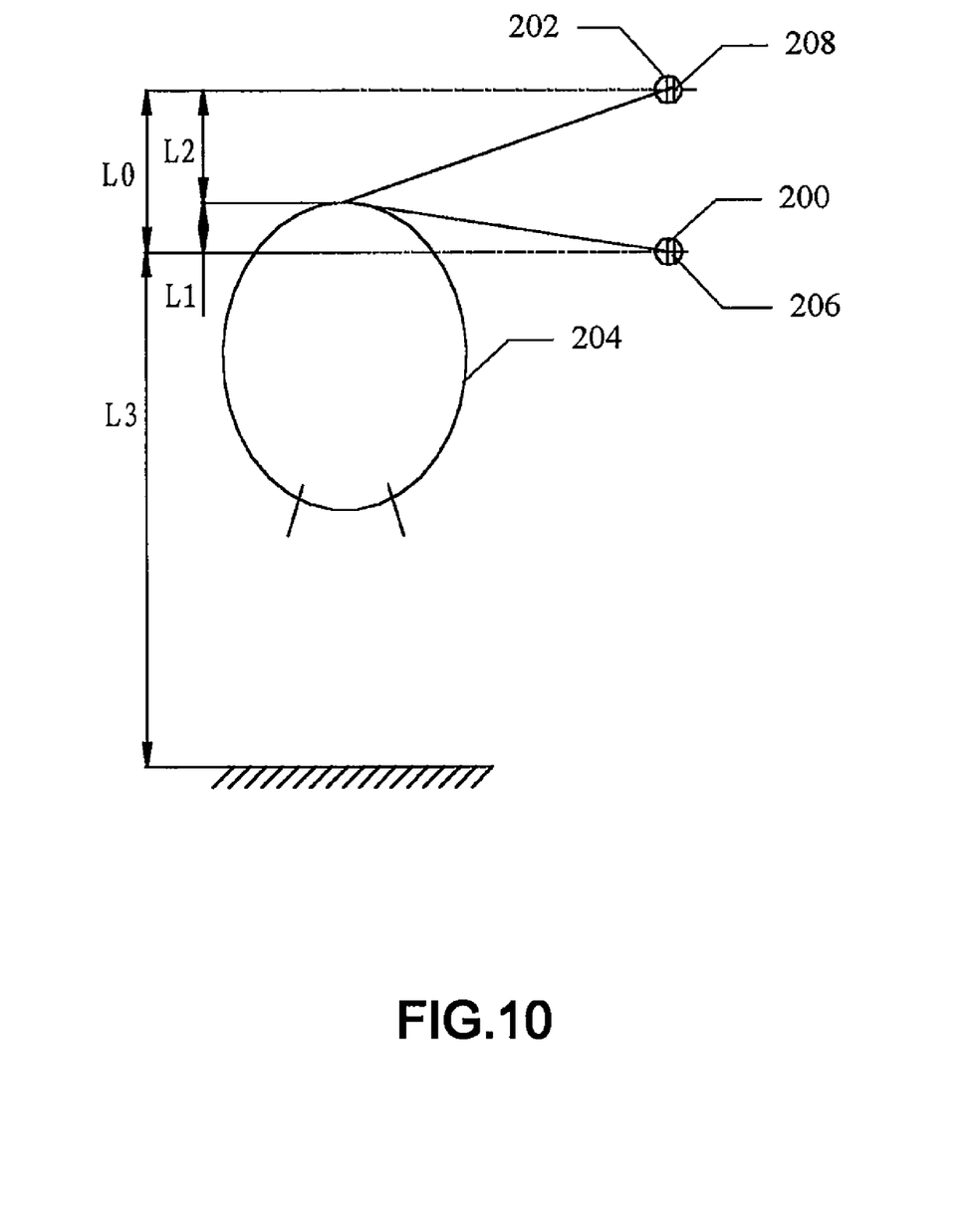
FIG. 10 is a schematic diagram of an optical body height measurement instrument according to another embodiment of the present invention.

As shown in FIG. 10, the optical height measurement instrument according to the embodiment comprises at least two lenses and a photosensitive sensor arranged in the image side of each lens. When the object to be measured is relatively tall, multiple lens, for example, three, four or five, may be spaced apart along the direction of the height of the measured object (i.e., in the vertical direction), so as to guarantee measurement accuracy. The height measurement instrument according to this embodiment will be illustrated below, taking two lenses as an example.

Figure 11:
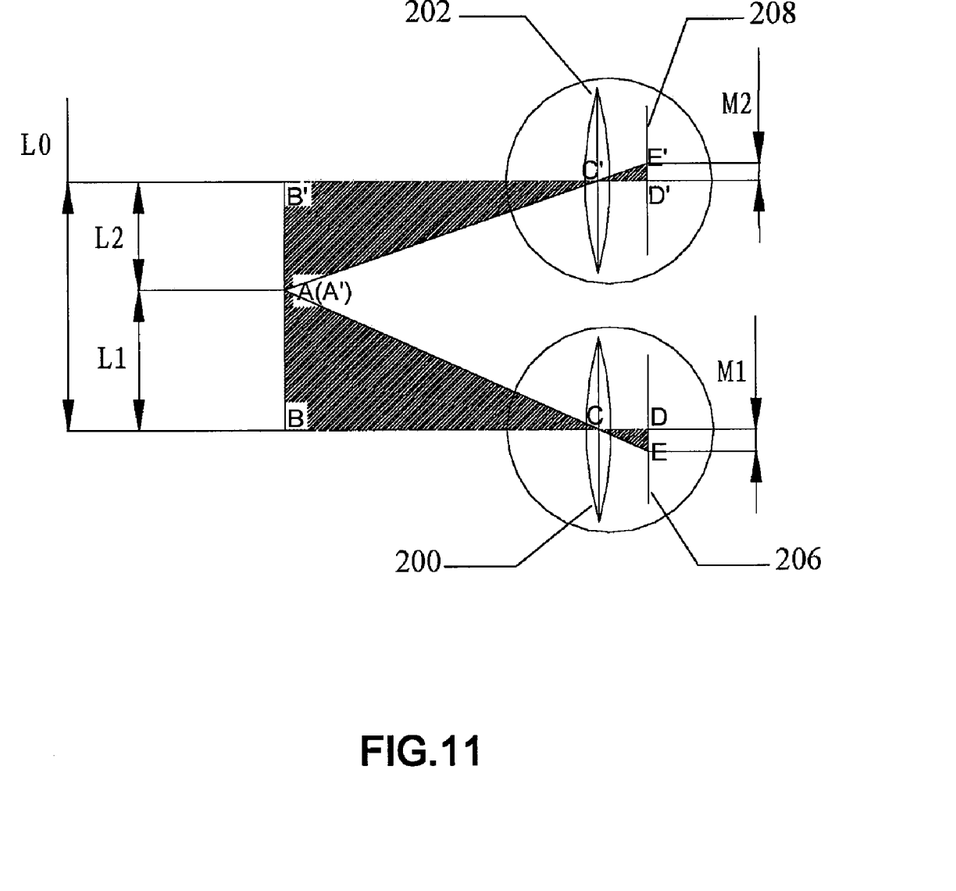
FIG. 11 is a schematic diagram of computation of the height of the object to be measured using the optical body height measurement instrument according to the another embodiment of the present invention.

As shown in FIG. 10, a first lens 200 and a second lens 202 are spaced from one another in the direction parallel to the height of the measured height (i.e., in the vertical direction). Photosensitive sensors 206 and 208 are positioned at the image sides of the lenses, respectively. The first lens 200 and the second lens 202 may be composed of a convex lens, or may be in the form of a pinhole or a slit arranged horizontally. In this embodiment, the photosensitive sensors 206 and 208 are preferably located on the image planes of the first lens 200 and the second lens 202 respectively, as shown in FIG. 11. The head of the object 204 to be measured is located between the first lens 200 and the second lens 202. The first lens 200 and the second lens 202 individually image the head of the object based on the infrared rays emitted therefrom, and the photosensitive sensors 206 and 208 individually sense the distance from the optical axis to the top of image as formed. Thereafter, the height of the object 204 to be measured is determined based on the distances as measured.

As shown in FIG. 11, the first lens 200 and the second lens 202 are located in the same vertical line with their optical axes parallel to each other. Thus, the following equation (1) may be derived:

$$BC=B'C', CD=C'D'; \quad (1)$$

Since the right triangle $\triangle ABC$ is similar to the right triangle $\triangle EDC$, then $$AB/DE=BC/DC, \text{ i.e., } L1/M1=BC/DC; \quad (2)$$

In a similar way, since the right triangle $\triangle A'B'C'$ is similar to the right triangle $\triangle E'D'C'$, then $$L2/M2=B'C'/D'C'; \quad (3)$$

Combining the equations (1), (2) and (3) gives:

$$L1/L2=M1/M2;$$

Since L1+L2=L0, it is possible to derive the equation L1/L0=M1/(M1+M2), i.e.

$$L1=(M1/(M1+M2))\times L0$$

Therefore, the height H of the object to be measured is:

$$H=L3+L1=L3+(M1/(M1+M2))\times L0.$$

It can be seen from the immediately above equation that the height of the object to be measured may be computed once distances M1 and M2 sensed by the photosensitive sensor are determined, since L0 and L3 are predetermined.

Figure 12:
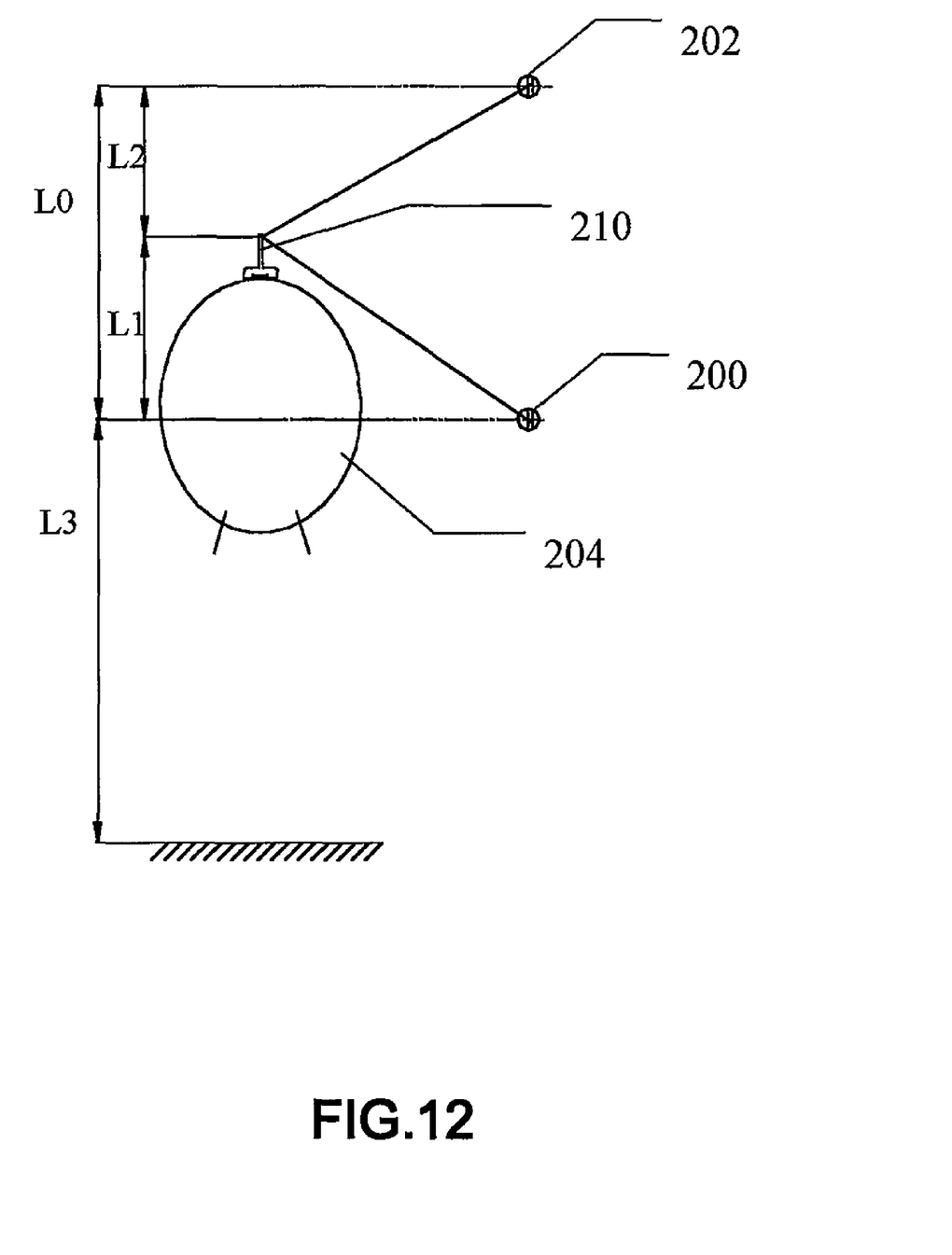
FIG. 12 is a schematic diagram of an optical body height measurement instrument using an auxiliary light source, according to another embodiment of the present invention.

In this embodiment, an auxiliary light source may also be used to perform the height measurement. The auxiliary light source has the same configuration as in embodiment 1. It also comprises a contact switch, as shown in FIG. 5. During the measurement, the auxiliary light source 210 may be placed on the head of the object to be measured. The auxiliary light source 210 emits light with a predetermined wavelength. The first lens 200 and the second lens 202 are thus able to form images using the emitted light. The photosensitive sensors 206 and 208 then sense respective images. As shown in FIG. 12, the distance between the first lens 200 and the second lens 202 is assumed to be L0; the distances of the auxiliary light source 210 from the first lens 200 and the second lens 202 are respectively assumed to be L1 and L2; the height of the first lens 200 is L3; the length of the auxiliary light source 210 is L4; and the distances between the images of the auxiliary light source 210 formed by the first lens 200 and the second lens 202 and the optical axes of the first lens 200 and the second lens 202 are respectively assumed to be M1 and M2. Likewise, the height H of the measured object may be determined as:

$$H = L3 + L1 - L4 = L3 - L4 + (M1/(M1+M2)) \times L0$$

Figure 13:
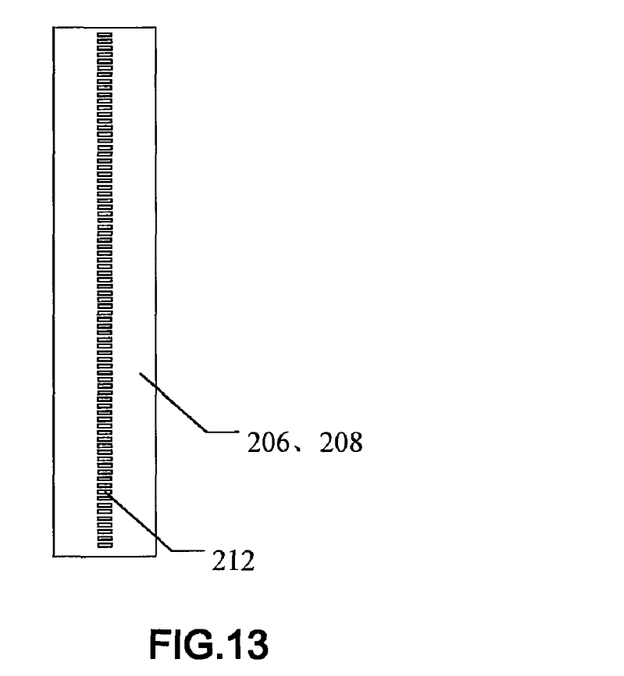
FIG. 13 is a schematic diagram of a photosensitive sensor composed of a single row of photosensitive elements.
Figure 14:
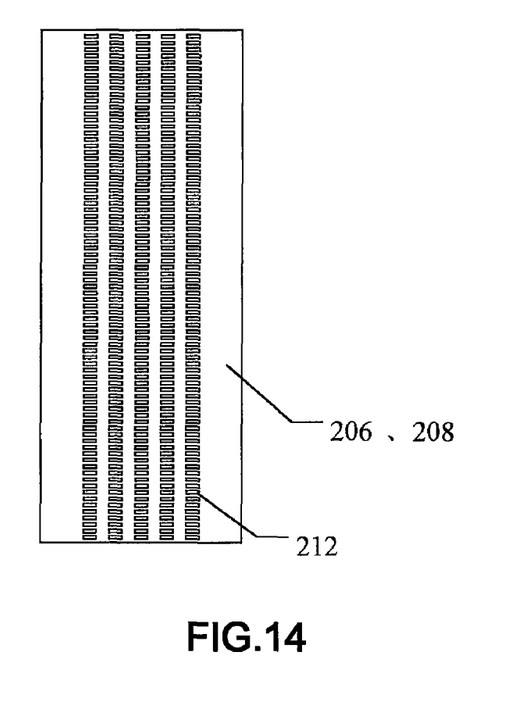
FIG. 14 is a schematic diagram of a photosensitive sensor composed of an array of photosensitive elements.

In this embodiment, the photosensitive sensors 206 and 208 may be composed of a single row of photosensitive elements 212 or an array of photosensitive elements 212, as shown in FIG. 13 or 14.

To reduce interference, filters 110 may be arranged on the optical path between the object 204 to be measured or the auxiliary light source 210 and the photosensitive sensors 206 and 208, so that only the infrared rays emitted from the head of the object 204 or the light with a predetermined wavelength emitted from the auxiliary light source 210 are allowed to pass. In this embodiment, the filters are preferably arranged in front of both of the photosensitive sensors 206 and 208.

The height measurement instrument according to the embodiment may also comprise a display unit coupled to the processing unit to display the measured results.

The height measurement instrument according to the embodiment may also comprise a driving device for driving the first lens 200 and the second lens 202, so that the head of the object to be measured or the auxiliary light source is located between the first lens 200 and the second lens 202. In this case, the height L3 of the first lens 200 may be determined in a similar way as in the embodiment 1. Accordingly, the height of the object to be measured may also be determined in the manner as described above.

Although the present invention has been described with reference to specific embodiments, it is not intended that the present invention be limited to those specific embodiments, and many modifications and variations may instead made to the present invention. In addition, terms such as "first", "second" etc. in this description and claims of this application shall not be construed as restrictive, but illustrative only.

What is claimed is:

1. An optical body height measurement instrument for measuring a height of an object, the optical body height measurement instrument comprising:

an auxiliary light source configured to be placed on the head of the object to be measured;

a lens configured to be movable along a direction parallel to the height of the object to be measured and form an image of the object and of the auxiliary light source;

a photosensitive sensor arranged at an image side of the lens to sense the formed image; and a driving device configured to drive the lens along a direction parallel to the height of the object, wherein when the lens is moved across the height at which the auxiliary light source is located, a hop occurs to an output of the photosensitive sensor; and wherein the height of the object is determined based on the height of the lens measured at the time of the occurrence of the hop and a distance between the auxiliary light source and the head of the object.

2. The optical body height measurement instrument according to claim 1, wherein the lens forms an image based on infrared rays emitted from the measured object, and the photosensitive sensor is adapted to sense the infrared image of the object.

3. The optical body height measurement instrument according to claim 1, wherein the auxiliary light source emits light with a predetermined wavelength, which is correspondingly sensed by the photosensitive sensor.

4. The optical body height measurement instrument according to claim 1, wherein the auxiliary light source further comprises: a contact switch configured to be closed to activate the auxiliary light source when the auxiliary light source is placed on the head of the object.

5. The optical body height measurement instrument according to claim 4, wherein the photosensitive sensor is arranged at the intersection of an image plane of the lens and the optical axis of the lens.

6. The optical body height measurement instrument according to claim 1, further comprising: a filter arranged in an optical path between the object and the photosensitive sensor such that only infrared rays emitted from the object or light with a predetermined wavelength emitted from the auxiliary light source are allowed to pass.

7. The optical body height measurement instrument according to claim 1, wherein the lens comprises at least one convex lens.

8. The optical body height measurement instrument according to claim 1, wherein the lens is in the form of a pinhole or a slit.

9. The optical body height measurement instrument according to claim 1, wherein when the lens is moved across the height at which the head of the object or the auxiliary light source is located, the photosensitive sensor starts to or not to detect formation of an image of the object or the auxiliary light source, which causes a hop.

10. The optical body height measurement instrument according to claim 1, further comprising:

a processing unit for computing the height of the object; and a display unit for displaying the measured height.

* * * * *